United States Patent [19]

Murashita et al.

[11] Patent Number: 5,515,849
[45] Date of Patent: May 14, 1996

[54] DIAGNOSTIC ULTRASOUND APPARATUS

[75] Inventors: Masaru Murashita; Hiroyuki Kawada; Toshiyuki Matsunaka, all of Mitaka, Japan

[73] Assignee: Aloka Co., Ltd., Japan

[21] Appl. No.: 377,389

[22] Filed: Jan. 24, 1995

[30] Foreign Application Priority Data

Jan. 25, 1994 [JP] Japan .................................. 6-006625
Sep. 28, 1994 [JP] Japan .................................. 6-232971

[51] Int. Cl.$^6$ .................................................. A61B 8/00
[52] U.S. Cl. .................................................. 128/660.07
[58] Field of Search ................. 128/660.04, 660.05, 128/660.07, 661.07, 661.08, 661.09, 661.10, 662.02, 916

[56] References Cited

U.S. PATENT DOCUMENTS

| | | | |
|---|---|---|---|
| 5,188,113 | 2/1993 | Sato et al. | 128/661.09 |
| 5,211,169 | 5/1993 | Freeland | 128/661.08 |
| 5,282,471 | 2/1994 | Sato | 128/660.07 |

Primary Examiner—George Manuel
Attorney, Agent, or Firm—Marger, Johnson, McCollom & Stolowitz

[57] ABSTRACT

A diagnostic ultrasound apparatus includes a displacement image data frame memory for storing, frame by frame, two-dimensional ultrasound image data of a living body to be observed; displacement image data sampling section for sampling displacement image data which is obtained by comparing two-dimensional ultrasound image data of a newest frame with the two-dimensional ultrasound image data of any one of the previous frames stored in the displacement image data frame memory, the displacement image data representing displacement in the living body between the compared frames; displacement hysteresis image forming section for forming displacement hysteresis image data which represents changes between the thus-formed plural displacement image data by sequentially combining the plural displacement image data with the lapse of time; and a display monitor for displaying a displacement hysteresis image on the basis of thus-produced displacement hysteresis image data. When this apparatus is used for diagnosing a heart, the displacement hysteresis image shows the state of movement of the living body such as the heart muscle with the lapse of time for the time interval from peak expansion of the heart ventricle to peak contraction thereof. In this case, since the width of the displayed displacement hysteresis image shows the amount of movement (activity) of the heart muscle, there is improved accuracy in diagnosing such things as abnormal movement in the heat and the position where the abnormal movement occurs.

23 Claims, 7 Drawing Sheets

DIAGNOSTIC ULTRASOUND APPARATUS

BACKGROUND OF THE INVENTION

1. Field of the Invention

The present invention relates to a diagnostic ultrasound apparatus, and more particularly to a diagnostic ultrasound apparatus for carrying out diagnosis and measurement of movement of living body tissue based on two-dimensional ultrasound image data.

2. Description of the Prior Art

In general, two-dimensional ultrasound images are used to inspect and measure abnormal movements of living body tissue, for example, abnormal movement of a cardiac muscle caused by the stenosis or a coronary artery. Here, a coronary artery means an artery which sends blood to heart tissue. In the case where a stenosis occurs in such coronary artery, the portion or a cardiac muscle receiving blood from such coronary artery does not get supplied with a sufficient amount or blood. For this reason, the movement of such cardiac muscle portion becomes lowered, and this gives rise to abnormal movement. Now, when a method of observing such abnormal movement is carried out using two-dimensional ultrasound images, the two-dimensional ultrasound image corresponding to the contraction stage (systole) or the expansion stage (diastole) of the heart ventricle are first displayed on a monitor. Then, the cross-sectional area of the heart ventricle is measured based on the obtained two-dimensional ultrasound image, and a certain value calculated from the thus-measured cross-sectional area value is compared with a prescribed reference value which shows normal condition, whereby the abnormal movement of the cardiac muscle is observed and measured based on the difference between the calculated value and the reference value.

Furthermore, there exists an X-ray image forming process as a method of inspecting stenosis of coronary arteries (coronary angiography). In such coronary angiography method, a catheter is first inserted directly into an artery of an arm or thigh, and then an image forming agent is passed into the coronary artery through the catheter. Then, an X-ray picture of the coronary artery is taken. The thus-obtained X-ray image is used to observe the stenosis of the coronary artery.

However, the prior art process of carrying out diagnosis of abnormal movement of the heart by measuring the cross-sectional area of the heart ventricle based on ultrasound images is quite complex and therefore requires much time to carry out such measurements, thus making it impossible to achieve the long-desired goal of shortening measurement time. Furthermore, because measurements of abnormal movement are carried out based on the difference between a prescribed reference value and the cross-sectional area value of a heart ventricle during the systole or diastole thereof, it is very difficult to identify the portion where abnormal movement occurs in the living body tissue. In particular, in the case where the amount or abnormal movement of the living body tissue is small, the change in cross-sectional area is also small, and this results in a low accuracy of detection.

Furthermore, in the coronary angiography method, since a catheter must be directly inserted into the blood vessel and X-rays must be passed through the living body, the level of safety of such method can not be considered to be sufficiently high.

SUMMARY OF THE INVENTION

It is an object of the present invention to overcome the problems of the prior art methods described above.

It is another object of the present invention to provide a diagnostic ultrasound apparatus which has a high level of safety and which can carry out highly accurate diagnosis of abnormal movement of living body tissue.

It is a further object of the present invention to provide a diagnostic ultrasound apparatus capable of easily and accurately determining such factors as the position, speed and extent of abnormal movements of living body tissue.

In order to achieve the objects stated above, time present invention has the structure described below.

Namely, a diagnostic ultrasound apparatus according to the present invention comprises a displacement image data frame memory for storing, frame by frame, two-dimensional ultrasound image data of a living body; displacement image data sampling means for sampling displacement image data which is obtained by comparing two-dimensional ultrasound image data of a newest frame with the two-dimensional ultrasound image data of any one of the previous frames stored in the displacement image data frame memory, the displacement image data representing displacement in the living body between the compared frames; displacement hysteresis image forming means for forming displacement hysteresis image data which represents changes between thus-formed plural displacement image data by sequentially combining the plural displacement image data with the lapse of time; and display means for displaying a displacement hysteresis image on the basis of the displacement hysteresis image data.

In the diagnostic ultrasound apparatus according to the present invention having the above construction, the displacement image data frame memory stores two-dimensional ultrasound image data frame by frame, and then the displacement image data sampling means compares two-dimensional ultrasound image data of the newest frame with the two-dimensional ultrasound image data of any one of the previous frames stored in the displacement image data frame memory and then samples only the portions of both data which are different from each other as the displacement image data. At this point, the sampled data, that is the displacement image data forms an image which shows the amount of displacement of the living body tissue within the time interval from the previous frame to the newest frame, namely a displacement image. Further, the displacement hysteresis image forming means sequentially combines these displacement images with the lapse of time, and by doing this the changes in the displacement images over a time interval relating to a plurality of frames, namely a displacement hysteresis image, is displayed on the display means such as a monitor.

Accordingly, when diagnosis is being carried out, for example, on abnormal movement of a cardiac muscle, it becomes possible to display the state of movement of the heart muscle with the lapse of time for the time interval from peak expansion of the heart ventricle to peak contraction of the ventricle. Furthermore, as the width of the displayed displacement hysteresis image shows the amount of movement (activity) of the living body tissue, there is improved accuracy in diagnosing such things as abnormal movement in the living body tissue and the position where the abnormal movement occurs.

As stated in the above, the diagnostic ultrasound apparatus according to the present invention samples only the amount of displacement of the living body tissue, namely data of the moving portion, and displays such data with the lapse of time, wherein the width of the displayed hysteresis image shows the amount of displacement (activity) of the living body tissue. Therefore, in comparison with prior art devices that measure the cross-sectional area of ultrasound images of living body tissue, the diagnostic ultrasound apparatus according to the present invention can detect with extreme sensitivity any abnormal movement of the living body tissue, the position where such abnormalities occur.

Furthermore, the diagnostic ultrasound apparatus according to the present invention is able to detect abnormal movement and the like of the living body tissue by simply transmitting ultrasound waves toward the living body tissue and receiving reflected ultrasound waves therefrom, and this eliminates the risk of injury to the living body tissue that had existed with prior art processes using the catheters that are liable to affect the coronary arteries.

Moreover, the diagnostic ultrasound apparatus according to the present invention makes it possible for an operator to place an ultrasound probe at any desired position of the living body being observed. Furthermore, because the processes that take place after positioning of the ultrasound probe will be carried out automatically by the diagnostic ultrasound apparatus itself, it becomes easy to carry out such operations and diagnosis can be carried out in a short amount of time.

In the present invention, it is preferred that the displacement image data is produced by comparing the two-dimensional ultrasound image data of the newest frame with the two-dimensional ultrasound image data of the previous frame just before the newest frame, and then sampling portions of both data which are different from each other. In this connection, it is also preferred that the displacement image data frame memory stores two-dimensional ultrasound image data of a plurality of previous frames, and the displacement image data is produced by comparing the two-dimensional ultrasound image data of the newest frame with the two-dimensional ultrasound image data of a fixed one of the previous frames, and then sampling portions of both data which are different from each other.

In the present invention, the displacement hysteresis image forming means includes displacement hysteresis image frame memory for storing the plural displacement image data, and means for adding each of the plural displacement image data stored in the displacement hysteresis image frame memory with a newest displacement image data supplied from the displacement image data sampling means to form the displacement hysteresis image data.

Further, in the present invention, it is preferred that the displacement hysteresis image forming means further includes means for imparting weighting on each of the plural displacement image data stored in the displacement hysteresis image frame memory for distinguishing each of the plural displacement image data. In this connection, it is more preferred that the two-dimensional ultrasound image data is formed from brightness data, and the weighting process is carried out so as to reduce the brightness value of the respective previous displacement image data gradually in comparison with that of the newest one.

In the present invention, it is preferred that the diagnostic ultrasound apparatus further comprises means for thresholding the two-dimensional ultrasound image data which is to be supplied to the displacement image data frame memory into binary-coded image data on the basis of a predetermined threshold value, and the displacement image data is formed from the binary-coded two-dimensional ultrasound image data. Use of such binary-coded image data makes it easy to compare the two-dimensional ultrasound data of the respective frames at the displacement data sampling means.

Further, it is also preferred the diagnostic ultrasound apparatus further comprises means for eliminating noise from the binary coded two-dimensional image data, and then outputting such noise-eliminated data to the displacement image data sampling means and the displacement image data frame memory.

In the present invention, it is preferred that the diagnostic ultrasound apparatus further comprises sampling control means for controlling the process time of the displacement image data sampling process carried out by the displacement image data sampling means. In this case, it is preferred that the processing time is synchronized with biological signals of the living body. Further, it is also preferred that the processing time is synchronized with the occurrences of the R-waves of a heart of the living body.

By controlling the process time of the displacement data sampling process as described above, it is possible to obtain a displacement image for any prescribed Interval of time. In particular, by synchronizing the sampling process time with the biological signal of the living body such as the R-waves of the heart, it becomes possible to easily and more accurately observe abnormalities in the direction of movement of the living body tissue, the amount of movement and the like.

In the present invention, it is also preferred that the diagnostic ultrasound apparatus further comprises means for setting at least one desired data sampling line for the displacement hysteresis image displayed on the display means, means for sampling ultrasound image data along the data sampling line from the displacement hysteresis image data constituting the displacement hysteresis image, and means for displaying the sampled data on the display means with the lapse of time as M-mode image.

By doing so, it becomes easy to make comparisons between the displayed regions coinciding with the designated lines with regard to direction and speed of movement, amount of movement and the like.

In this case, it is also preferred that the diagnostic ultrasound apparatus further comprises means for measuring the width of the M-mode image at a designated time axis which shows the amount of the displacement along the data sampling line at tiler time. By doing so, it becomes possible to quantize the movement of the living body tissue. For example, it becomes possible to automatically obtain ratios between the width of one region of the displacement hysteresis image along a designated line, namely the speed and amount of movement for that region, and the width of other regions, thus making it possible to quantize the movement data.

The diagnostic ultrasound apparatus according to the present invention can also be constructed from: means for recording, frame by frame, two-dimensional ultrasound image data obtained by transmitting and receiving ultrasound waves to and from an object to be observed of a living body; means for producing displacement image data on the basis of two-dimensional ultrasound image data of a newest frame and the two-dimensional ultrasound image data of any one of the previous frames stored in the recording means, the displacement image data representing the displacement of the object between the newest frame and said previous frame; means for producing composite image data which represents the amount of the movement of the object to be observed for a certain period, by sequentially combining the thus-obtained plural displacement image data for the certain time period, and means for displaying a composite image on the basis of said visual image data.

Further, the diagnostic ultrasound apparatus according to the present invention can also be constructed from: means for recording, frame by frame, two-dimensional ultrasound image data of different stages of movement of an object to be observed of a living body; means for producing composite ultrasound image data which can represent the movement of the object for a certain time period, the composite ultrasound image data being formed by using the ultrasound image data recorded in the recording means and two-dimensional ultrasound image data of a newest frame; and means for displaying the thus-produced composite ultrasound image.

Another aspect of the present invention is directed to a method of observing a living body with ultrasound waves, This method comprises the steps of: transmitting and receiving ultrasound waves to and from a living body to be observed; recording, frame by frame, two-dimensional ultrasound image data obtained from the received ultrasound waves into a frame memory; producing displacement image data by comparing two-dimensional ultrasound image data of a newest frame with the two-dimensional ultrasound image data of any one of the previous frames stored in the frame memory, thus forming displacement image data constituting a displacement image which represents the displacement amount of the object between these frames; producing displacement hysteresis image data which represents changes of the object between the plural displacement images by sequentially combining the plural displacement images with the lapse of time; and displaying thus-formed displacement hysteresis image data on a monitor for the purpose of observation. In this case, it is preferred that the method further comprises the step of changing the brightness of each of the displacement images.

The other aspect of the present invention is directed to a method of diagnosing a heart of a patient with ultrasound waves. This method comprises the steps of: producing a plurality of B-mode image data of the heart of the patient to be diagnosed, and storing these image data into a frame memory; producing displacement image data which represents the displacement of a cardiac muscle of the heart by using B-mode image data of a newest frame and any one of the previous B-mode image data stored in the frame memory; combining thus-obtained displacement image data into one image data to form a composite image which represents the the movement of the cardiac muscle for a certain period, in which a portion of the heart having a small movement is indicated by a small width; and inspecting the condition of the heart of the patient on the basis of the composite image.

Further, a diagnostic ultrasound apparatus according to the present invention can be constructed from: means for obtaining B-mode image data by transmitting and receiving ultrasound waves to and from an object of a living body to be observed; means for producing composite image data which represents the displacement of the object for a certain period, the composite image data being obtained by sequentially combining thus-obtained plural B-mode image data with the lapse of time for the certain period; and means for displaying thus-formed composite image data as a composite image.

In this case, it is preferred that the diagnostic ultrasound apparatus further includes means for thresholding the B-mode image data into binary-coded image data. It is also preferred that the diagnostic ultrasound apparatus further includes: frame memory means for recording the plural binary-coded B-mode image data frame by frame; and means for producing displacement image data which represents displacement of the object between any one of the previous frame and a newest frame, the displacement image data being formed on the basis of the B-mode image data of the previous frame stored in the frame memory and B-mode image data of the newest frame; wherein thus-obtained a plurality of the displacement image data being sequentially combined for the time period to form the composite image data. In this case, it is also preferred that the diagnostic ultrasound apparatus further includes means for distinguishing each of the plural displacement image data which form said composite image data.

Other objects, structures and advantages of the present invention will become more apparent when the following detailed description of the preferred embodiments are taken into account in conjunction with the appended drawings.

DETAILED DESCRIPTION OF THE PREFERRED EMBODIMENTS

With reference to the appended drawings, a detailed description of the preferred embodiments of the present invention will now be given below.

EMBODIMENT 1

Figure 1:
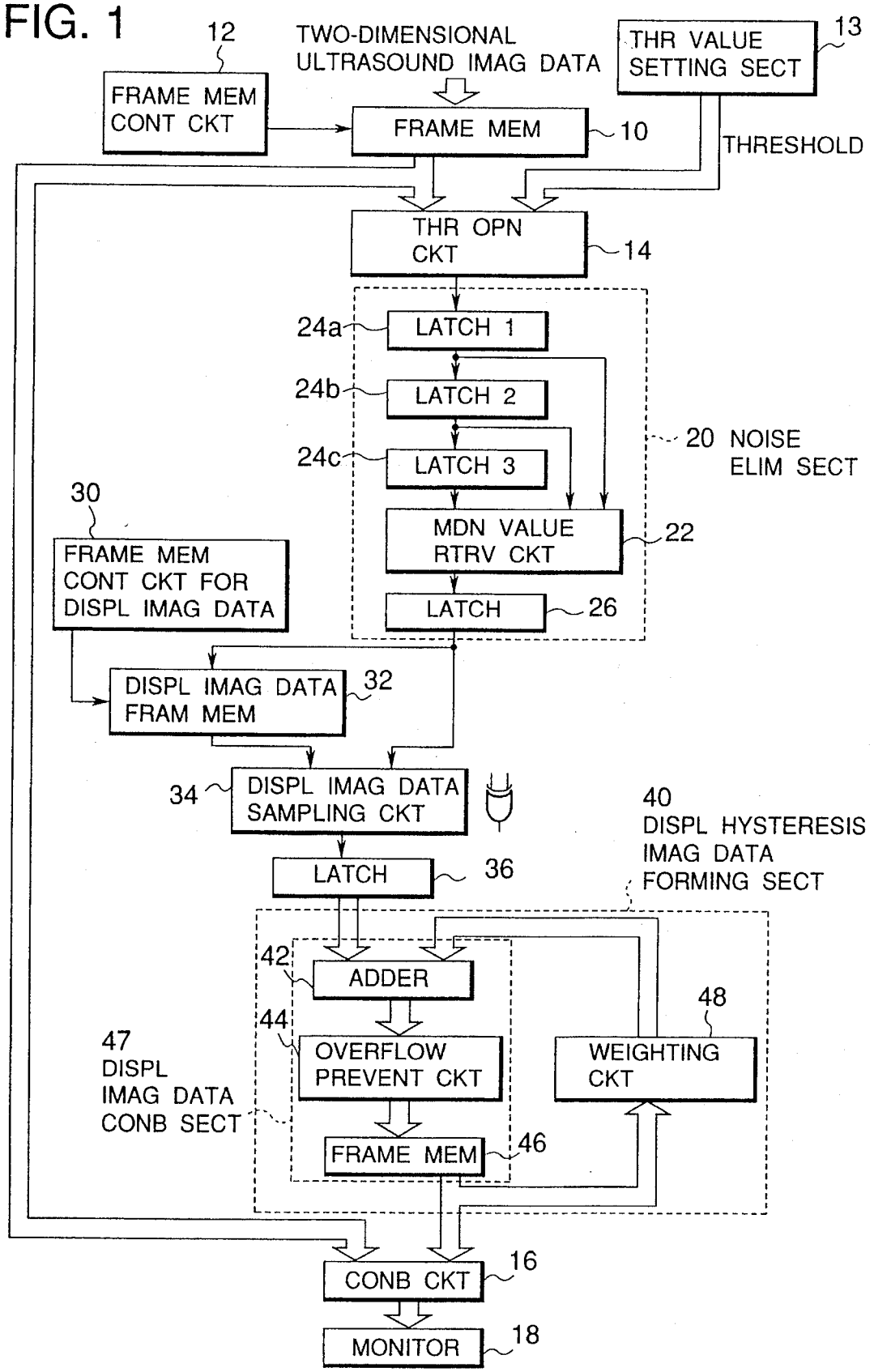
FIG. 1 is a block diagram showing the essential portions of a first embodiment of a diagnostic ultrasound apparatus according to the present invention.

FIG. 1 is a block diagram of a first embodiment of a diagnostic ultrasound apparatus according to the present invention.

A frame memory 10, of a type which is well-known in the art, is provided for storing two-dimensional ultrasound image data (commonly referred to as 'B-mode image data', and hereinafter in this application simply referred to as 'ultrasound image data') of a living body obtained from an ultrasound probe (not shown in the drawing). Such data is stored in the frame memory 10 frame by frame in the form of brightness data, and the frame memory is controlled by a frame memory control circuit 12. Further, a threshold operation circuit 14 is provided for thresholding or separating ultrasound image data outputted from the frame memory 10 into binary-coded image data (1 or 0) based on a predetermined threshold value set by a threshold value setting section 13. The threshold operation circuit 14 is constructed from a comparator or the like. A noise eliminating section 20 is provided for eliminating the noise of the ultrasound image data which have been binary-coded. This noise eliminating section 20 is comprised of a plurality of latch circuits 24a, 24b, 24c and a median value retrieval circuit 22 provided for retrieving a median value, and a latch circuit 26.

A displacement image data frame memory 22 is provided for storing frame by frame the binary-coded image data outputted from the noise eliminating section 20. The data stored in the displacement image data frame memory 82 is outputted to an displacement image data sampling circuit 34. Further, the displacement image data frame memory 32 is controlled by an displacement image data frame memory control circuit 30.

The displacement image data sampling circuit 84 compares the ultrasound image data of the newest frame which is outputted directly to the displacement image data sampling circuit 34 from the noise eliminating section 20 with the ultrasound image data of the most recent frame which is outputted to the displacement image data sampling circuit 34 after having been stored in the displacement image data frame memory 32, and then samples as displacement image data only those parts of the ultrasound image data that are different from each other. The displacement image data sampling circuit 34 is constructed from, for example, an exclusive OR circuit or the like. A latch circuit 36 is provided at the output side of the displacement image data sampling circuit 34. This latch circuit 38 first latches the displacement image data that has been sampled by the displacement image data sampling circuit 34 and then outputs this data at a prescribed timing to an adder 42 of an displacement hysteresis image data forming section 40.

The displacement hysteresis image data forming section 40 combines the displacement image data sequentially with the lapse of time so as to form displacement hysteresis image data. To carry out such composite data formation, the displacement hysteresis image data forming section 40 is comprised of an displacement image data combining section 47 and a weighting circuit 48. The displacement image data combining section 47 is comprised of the adder 42, an overflow prevention circuit 44 and a displacement hysteresis image frame memory 48. Here, the weighting circuit 48 weighs the previous displacement image data. The weighted displacement image data is then supplied to the adder 42.

A combining circuit 16 is provided for combining, when necessary, the displacement hysteresis image data formed by the displacement hysteresis image data forming section 40 with the ultrasound image data of a living body stored in the frame memory 10 (B-mode image data). Further, a monitor 18 which acts as a display means is used for simultaneously displaying, on separate regions thereof, two-dimensional ultrasound images (B-mode images) of a living body and displacement hysteresis images formed based on the displacement hysteresis image data, like those shown in FIG. 2 and FIG. 3.

An explanation of the operation of the diagnostic ultrasound apparatus according to the present embodiment will now be given below.

First, ultrasound waves are transmitted from an ultrasound probe (not shown in the drawings) to an object to be observed in a living body and reflected ultrasound waves (echoes) are received by the ultrasound probe. The received ultrasound waves are converted into digital signals which form ultrasound image data of the object being observed, and then such ultrasound image data of the object in the form of brightness data is stored sequentially frame by frame in the frame memory 10.

The ultrasound image data is then outputted from the frame memory 10 and inputted into the threshold operation circuit 14 and the combining circuit 16, respectively. The threshold operation circuit 14 thresholds (separates) the ultrasound image data outputted from the frame memory 10 into binary-coded image data (brightness data) by comparing it with a predetermined threshold value set by the threshold value setting section 18. By carrying out this binary-coded process. It becomes possible to clearly display an outline of a specific portion of tissue of the living body in the ultrasound image.

For example, in the case where the specified tissue is a cardiac muscle, it is possible to clearly distinguish between the cardiac muscle and a heart ventricle (blood) in the ultrasound image. In general, because there is a high percentage of reflected ultrasound waves for cardiac muscle tissue and the like, the brightness value of the obtained ultrasound image data is high. On the other hand, as the percentage of reflected ultrasound waves for blood is low relative to the percentage of reflected ultrasound waves for cardiac muscle tissue and the like, the brightness value of the obtained ultrasound image data for blood is relatively low. Accordingly, by setting a threshold value that is lower than the brightness value of the ultrasound image data obtained from cardiac muscles and higher than the brightness value of ultrasound image data obtained from blood, it is possible to clearly distinguish a cardiac muscle from blood, thereby making it possible to form a clear outline of the cardiac muscle. In this connection, the threshold value setting section 13 is constructed so as to be capable of setting variable thresholds.

Next, the noise eliminating section 20 carries out a noise elimination process on the binary-coded ultrasound image data. First, the latch circuits 24a, 24b, 24c latch binary-coded ultrasound image data (brightness data) corresponding to their three respective adjacent picture elements (pixels) on the image plane. The latched data is then outputted to the median value retrieval circuit 22. Here, the three picture elements are, for example, a series of three picture elements running in the horizontal or vertical directions. Next, the median value retrieval circuit 22 compares the data value (1 or 0) corresponding to the middle picture element with the predominant data value (1 or 0) of the three picture elements (here, the predominant data value means the data value that is the same for more than half of all the picture elements). In the case where the data value (1 or 0) of the middle picture element is different from the predominant data value of the three picture elements, the data value of the middle picture element is corrected so as to have the same value as the predominant data value. In this connection, it is to be understood that the number of latches is not limited to the three described above. For example, five latch circuits or latch circuits of 3×3 matrix or the like can be used. In these cases, it is also possible to carry out correction of data even when there is noise across a plurality of picture elements.

The binary-coded ultrasound image data that is outputted from the noise eliminating section 20 is directly inputted into the displacement image data sampling circuit 34. Further, the binary-coded ultrasound image data is also inputted into the displacement image data frame memory 32 simultaneously. In the displacement image data frame memory 32, the binary-coded ultrasound image data is stored frame by frame. The displacement image data frame memory 32 not only stores binary-coded image data of the newest frame, but also outputs the recorded binary-coded ultrasound image data of the frame just before the newest frame to the displacement image data sampling circuit 34

The displacement image data sampling circuit 34 compares the binary-coded ultrasound image data of the frame just before the newest frame outputted from the displacement image data frame memory 32 to the displacement image data sampling circuit 34 with binary-coded ultrasound image data of the newest frame directly inputted into the displacement image data sampling circuit 34 from the noise eliminating circuit 20. Then, the displacement image data sampling circuit 34 samples in the form of displacement image data only those parts of the image data that are different from each other. In this case, when the tissue of the living body under observation moves during the time between the newest frame and the frame just before the newest frame, the data of such partial movement will be in the form of a partial difference between the brightness data of the frame just before the newest frame and the brightness data of the newest frame. Therefore, by sampling the data of this partial difference, it is possible to sample the amount of displacement of the living body tissue in the form of displacement image data.

Now, when a previous frame is compared with the newest frame, such previous frame need not be the frame just before the newest frame, as described above, but instead can be any one of the previous frames. For example, In the case where a plurality of binary-coded ultrasound image data of a plurality of frames are stored in the displacement image data frame memory 32, a comparison can be made in the displacement image data sampling circuit 34 between binary-coded ultrasound image data of the newest frame and the binary-coded ultrasound image data of any one of the plurality of previous frames. Further, it is also possible to keep binary-coded ultrasound image data of the oldest frame recorded within the displacement image data frame memory 32, and then use the binary-coded ultrasound image data of this frame as a base. In this case, a comparison can be continually carried out between the binary-coded ultrasound image data of this oldest frame and the binary-coded ultrasound image data of the newest frame.

The newest displacement image data that has been sampled is latched by the latch circuit 36, and then at a prescribed timing, this displacement image data is inputted into the adder 42 of the displacement hysteresis image data forming section 40. Further, this displacement image data is stored in the displacement hysteresis image frame memory 46 via the overflow prevention circuit 44. The image data stored in the displacement hysteresis frame memory 46 is then outputted to the weighting circuit 48 and the combining circuit 16. The weighting circuit 48 then weighs (namely, reduces) the brightness value of the previous displacement hysteresis image data stored in the displacement hysteresis image frame memory 46 so as to make such brightness value smaller than the brightness value of the newest displacement image data. This weighted displacement image data is then outputted to the adder 42. In the adder 42, the displacement image data weighted by the weighting circuit 48 is added to the newest displacement image data inputted to the adder 42 from the latch circuit 36, to form a displacement hysteresis image data. Thus, when the reduced previous displacement image data is added in the adder 42 to the newest displacement image data, the brightness allows the newest displacement image to be clearly and emphatically displayed when the displacement hysteresis image is being displayed on the monitor 18. In this way, weighting can be carried out mainly for setting the display condition of the displacement hysteresis data to be displayed on the monitor 18. Accordingly, weighting need not be limited to a reducing process, but instead may also be carried out by performing an adding process. Further, it is also possible to have the display color change for each displacement image or to have a colorization process be carried out for the entire displacement hysteresis image.

Now, when thus-produced displacement image data are being combined, if a simple addition is taken place in the adder 42, there is a case that the brightness value of the added displacement hysteresis image data becomes so high at certain places to exceed the brightness value that is capable of being displayed. Thus, in order to prevent such problems, an overflow prevention circuit 44 is provided as shown in the drawing. Namely, the overflow prevention circuit 44 carries out a specific process at the regions where the brightness value exceeds the allowed limit. For example, the overflow prevention circuit 44 can carry out a process that changes the excessive brightness of all such regions to the maximum brightness value capable of being displayed.

When the newest displacement image data is combined with previous displacement image data, the combined image data is first stored in the displacement hysteresis image frame memory 48. Then, in the weighting circuit 48, weighting is once again carried out on the combined displacement image data (the displacement hysteresis image data while being combined) comprised of each of the previous displacement image data. The weighted image data is then added at the newest displacement image data supplied to the adder 42 at time next time period. In this way, the displacement image data can be combined with the lapse of time to form the displacement hysteresis image data. Then, when necessary, the ultrasound image data stored in the frame memory 10 (B-mode image data) can be combined in the combining circuit 16 with the thus-formed displacement hysteresis image data in order to display the ultrasound image and the displacement hysteresis image at separate regions on the monitor 18.

Figure 2:
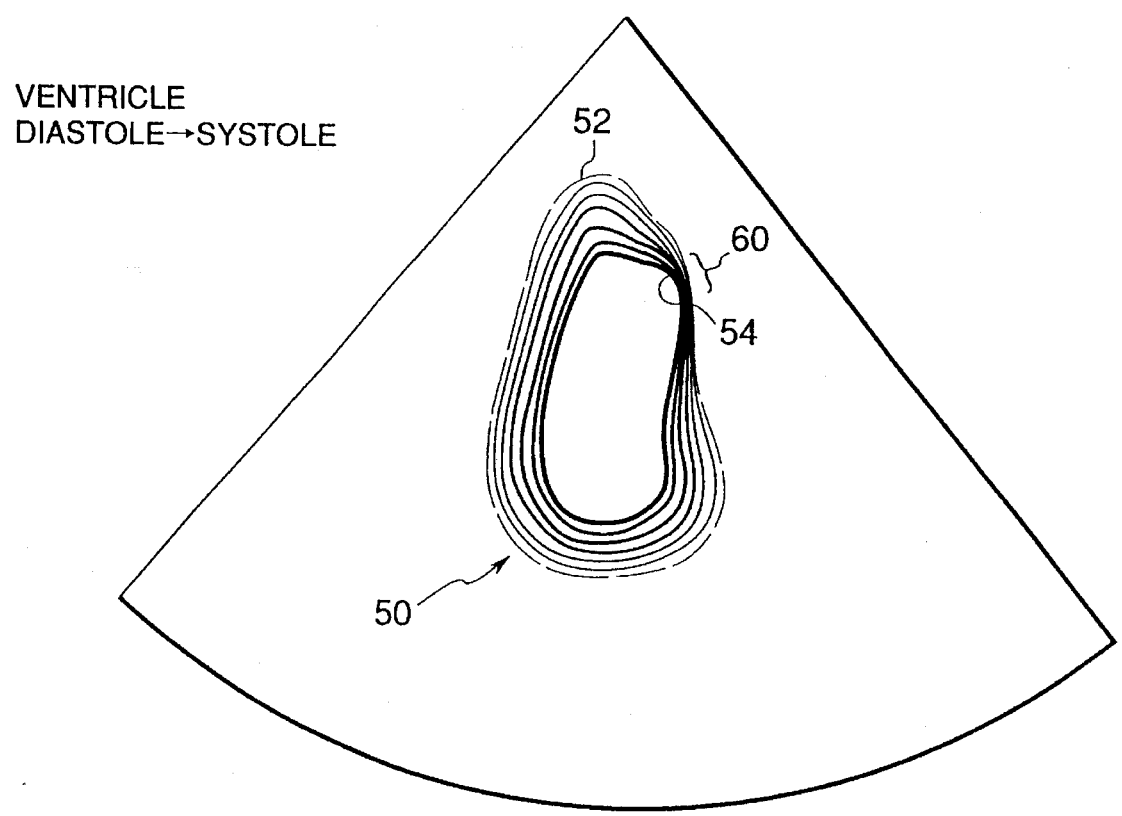
FIG. 2 is an example display of a displacement hysteresis image of a heart muscle from the time of peak expansion of a heart ventricle (diastole) to the time of peak contraction of the heart ventricle (systole) relating to the first embodiment of the present invention.

Next, the display results of the displacement hysteresis image will be explained with reference to FIG. 2 and FIG. 3. FIG. 2 shows an example display of a displacement hysteresis image of a cardiac muscle during a period from peak expansion in diastole of a ventricle to peak contraction in systole of the ventricle. As shown in FIG. 2, displayed at the outermost part of a displacement hysteresis image 50 is a displacement image 52 of the initial stage of the systole (contraction). In this case, the displacement image 52 has the lowest brightness among all the displacement images of the displacement hysteresis image 50. As the contraction of the heart ventricle progresses (i.e., as time elapses), the displacement images are displayed further and further toward the inside of the displacement hysteresis image 50 with increasing brightness. The inner most displacement image corresponds to the newest frame of the still progressing contraction, and so no brightness reduction, namely no weighting, has been carried out on the displacement image As such, the displacement image 54 has the highest brightness among the displacement images in the displacement hysteresis image 50. Now, in FIG. 2 each displacement image is represented by a line for the sake of simplification, but when actually displayed, each displacement image has a band-like shape with a width that corresponds to the amount of movement of the heart muscle or the like that occurred between successive frames. Also, these different brightness level band-like shaped displacement images are displayed mutually adjacent to each other and together form the displacement hysteresis image.

In this way, the amount of movement of the cardiac muscle is shown with the lapse of time in the displacement hysteresis image 50 of the cardiac muscle. For the places in the cardiac muscle where the amount of movement during contraction is quite small, each displacement image roughly overlaps with the other displacement images, as shown for the region 60 in FIG. 2. Accordingly, by observing such a region 60, an operator can easily discover the parts of the cardiac muscle where abnormal movement occurs. Furthermore, by observing such a region 60, it becomes possible to infer that an abnormality (e.g., stenosis) would exist in a coronary artery that supplies blood to the region 60 of the cardiac muscle.

Figure 3:
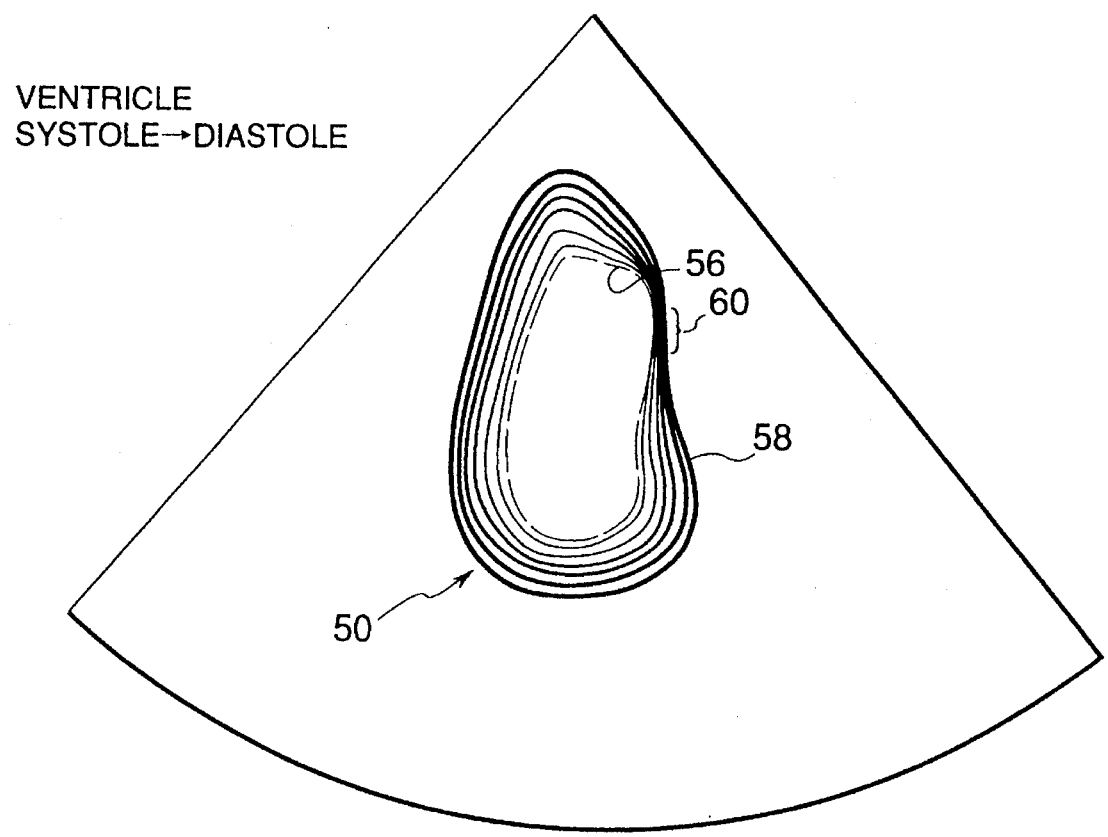
FIG. 3 is an example display of a displacement hysteresis image of a heart muscle from the time of peak contraction of a heart ventricle to the time of peak expansion of the heart ventricle relating to the first embodiment of the present invention.

FIG. 3 shows an example display of a displacement hysteresis image of a cardiac muscle during a period from peak contraction in systole of a ventricle to peak expansion in diastole of the ventricle. In other words, FIG. 3 shows a state of progression that is opposite to that shown in FIG. 2, and so the inner most displacement image 56 corresponding to the initial stage of expansion is displayed with the lowest brightness level among the displacement images of the displacement hysteresis image 50. And in reverse order to the situation described above, as the expansion of the heart ventricle progresses, the displacement images are displayed further and further toward the outside of the displacement hysteresis image 50 with increasing brightness. In this case, an outermost displacement image 58 corresponds to the newest frame of the still progressing expansion, and so no brightness reduction, namely no weighting, has been carried out on the outermost displacement image 58. As such, the displacement image 58 has the highest brightness among the displacement images in the displacement hysteresis image 50.

In the same way as FIG. 2 illustrated for the contraction situation described above, the region 60 in FIG. 3 shows the places in the cardiac muscle where the amount of movement during expansion is quite small, and therefore each displacement image roughly overlaps with the other displacement images.

In this way, the diagnostic ultrasound apparatus according to the present embodiment is able to display the amount of displacement of the living body tissue, namely it is able to sample only the portion that is moving and display such portion with the lapse of time. In this case, it should be noted that the width of the displacement portion of the displayed displacement hysteresis image shows the amount of movement (activity) of the living body tissue. Accordingly, in comparison which prior art apparatuses that measured the cross-sectional area of living body tissue on a B-mode image, the diagnostic ultrasound apparatus according to the present embodiment can detect abnormal movement of the living body tissue with extreme sensitivity and makes it extremely easy to identify the positions where abnormalities occur.

Furthermore, as the diagnostic ultrasound apparatus according to the present embodiment is able to detect abnormal movement and activity of the living body tissue by simply transmitting ultrasound waves toward the living body tissue and receiving reflected ultrasound waves therefrom, it is possible to eliminate the risk off injury to the living body tissue that had existed with prior art processes using catheters that are liable to affect the coronary arteries. Therefore, the diagnostic ultrasound apparatus according to the present embodiment is extremely safe for use with living body tissue.

Moreover, the diagnostic ultrasound apparatus according to the present embodiment makes it possible for an operator to place an ultrasound probe at any desired position of the living body being examined, because the processes that take place after positioning of the ultrasound probe will be carried out automatically by the diagnostic ultrasound apparatus itself. Therefore, it becomes easy to carry out such operations, and diagnosis can be carried out in a short amount of time.

In the present embodiment, displacement image data was sampled after a binary-coded process and a noise eliminating process were carried out on two-dimensional ultrasound image data of a living body. However, these processes are not always necessary. In the case where the binary-coded process is omitted, a circuit which can compare analog data may be used as the displacement image data sampling circuit.

Further, in the present embodiment, as described above, displacement images are first produced from the two-dimensional ultrasound images of the living body to be observed, and then the displacement hysteresis image is formed from the displacement images. However, it is also possible to produce a composite image which represents the changes in the B-mode images of the living body by sequentially combining a plurality of binary-coded ultrasound image data (B-mode image data) without omitting the process for producing the displacement images. In this case, the block diagram of FIG. 1 can be simplified so that the binary-coded B-mode image data is outputted from the noise elimination section 20 and then directly inputted to the adder 42 of the displacement hysteresis image data forming section 40 through a latch circuit.

EMBODIMENT 2

The feature of this embodiment is to further provide a circuit which can control the period or time in which the displacement image data sampling process is carried out. A detailed description of this embodiment is given below with reference to FIG. 4. For this embodiment, elements that are the same as or similar to those described for the the first embodiment will be designated by the same reference numerals and therefore a detailed description of such elements will be omitted.

Figure 4:
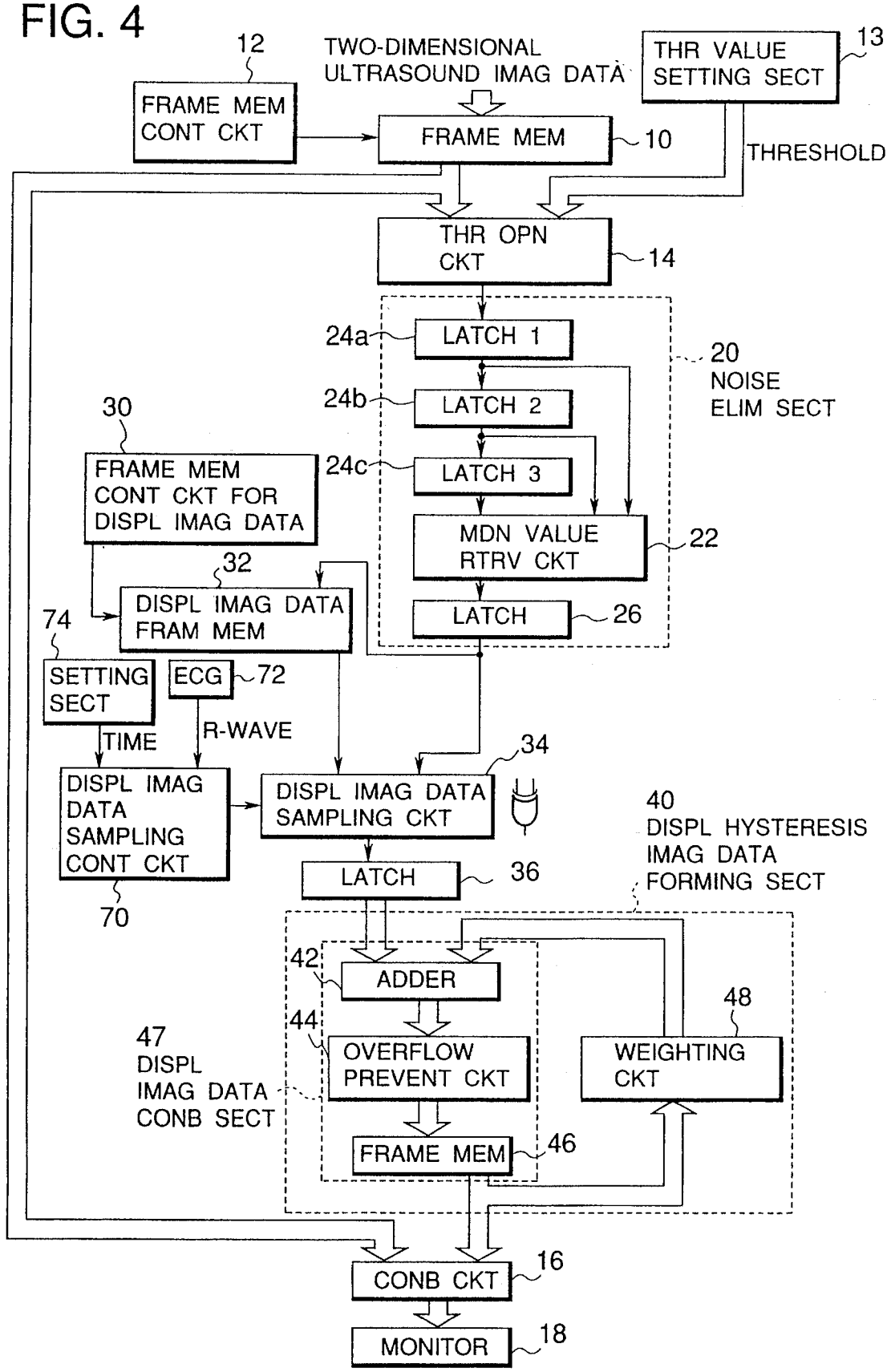
FIG. 4 is a block diagram showing the essential portions of a second embodiment of a diagnostic ultrasound apparatus according to the present invention.

As shown in FIG. 4, a displacement image data sampling control circuit 70 is connected to the displacement image data sampling circuit 34. Further, In order to set the sampling process time, an electrocardiograph (ECG) 72 and a setting section 74 are connected to the displacement image data sampling control circuit 70. In the displacement image data sampling circuit 34, the period of time in which the displacement image data sampling process is carried out is controlled in accordance with a control signal outputted from the displacement image data sampling control circuit 70.

In order to set the sampling process time, reference data such as the sampling process start time, process time, end time and the like are supplied to the displacement image data sampling control circuit 70 from the electrocardiograph 72 and the setting section 74. The displacement image data sampling control circuit 70 then generates control signal based on this reference data, and these control signals are inputted into the displacement image data sampling circuit 34. Then, in accordance with the control signals, the sampling process time period in the displacement image data sampling circuit 34 is controlled. Thus, it is possible to carry out a displacement image sampling process within the most appropriate sampling process time in accordance with the particular regions to be diagnosed and the purpose of diagnosis.

In the case where a cardiac muscle is being diagnosed, electrocardiogram waveform data, obtained for example based on the occurrence of an excitation of a cardiac muscle, is supplied to the displacement image data sampling control circuit 70 from the electro-cardiograph 72. At the same time, the sampling process time set with the setting section 74 by an operator or the like is supplied to the displacement image data sampling control circuit 70. In accordance with these signals, the displacement image data sampling control circuit 70 sets the sampling process start time so as to synchronize with the timing of the occurrence of the R-wave of the electrocardiogram waveform. Then, after the set sampling process time has elapsed, the displacement image data sampling control circuit 70 generates a prescribed control signal to terminate the sampling process and then outputs this signal to the displacement image data sampling circuit 34.

In the situation described above, the electrocardiogram R-wave form is a biological signal obtained by an electrical excitation of a heart ventricle. This timing of the R-wave occurrence corresponds to the moment when the heart ventricle is at peak expansion. Accordingly, by setting the starting time of displacement image data sampling process so as to synchronize with the occurrence of the R-wave. It is possible to display on the monitor 18 a displacement hysteresis image which continually shows the displacement from the peak expansion in the diastole.

Furthermore, in a general electrocardiogram waveform, the same waveform is repeated every heart beat. For this reason, the difference between waveforms of each heart beat is extremely small, and so there is a high repeatability of waveform data. Moreover, when the average person is diagnosed, there can be seen the features that the dispersion of waveform data is small and there is a high uniformity of such waveform data. For example, if the sampling process time period is set to be half the time of each R-wave interval (0.5 seconds for the average person), the displacement image data sampling process will be selectively carried out only for the time from the peak expansion to the peak contraction of the heart ventricle for each heart beat.

Thus, the structure of the present embodiment makes it possible to continually obtain displacement hysteresis images for the period from the peak expansion to the peak contraction of the heart ventricle, namely displacement hysteresis images that follow one specified direction of movement of the cardiac muscle so that no image becomes displayed in the reverse direction over a previously displayed image. Accordingly, the present embodiment is extremely efficient at detecting abnormalities in the direction of movement of the cardiac muscle, such as when one portion of the heart wall has an abnormal movement that causes it to protrude outward (dyskinesis). Furthermore, it becomes possible to obtain accurate data on the amount of displacement of the living body tissue.

EMBODIMENT 3

The feature of this embodiment is to further provide a circuit that can sample ultrasound image data along any desired straight line on the displacement hysteresis image. A detailed description of this embodiment is given below with reference to FIG. 5.

Figure 5:
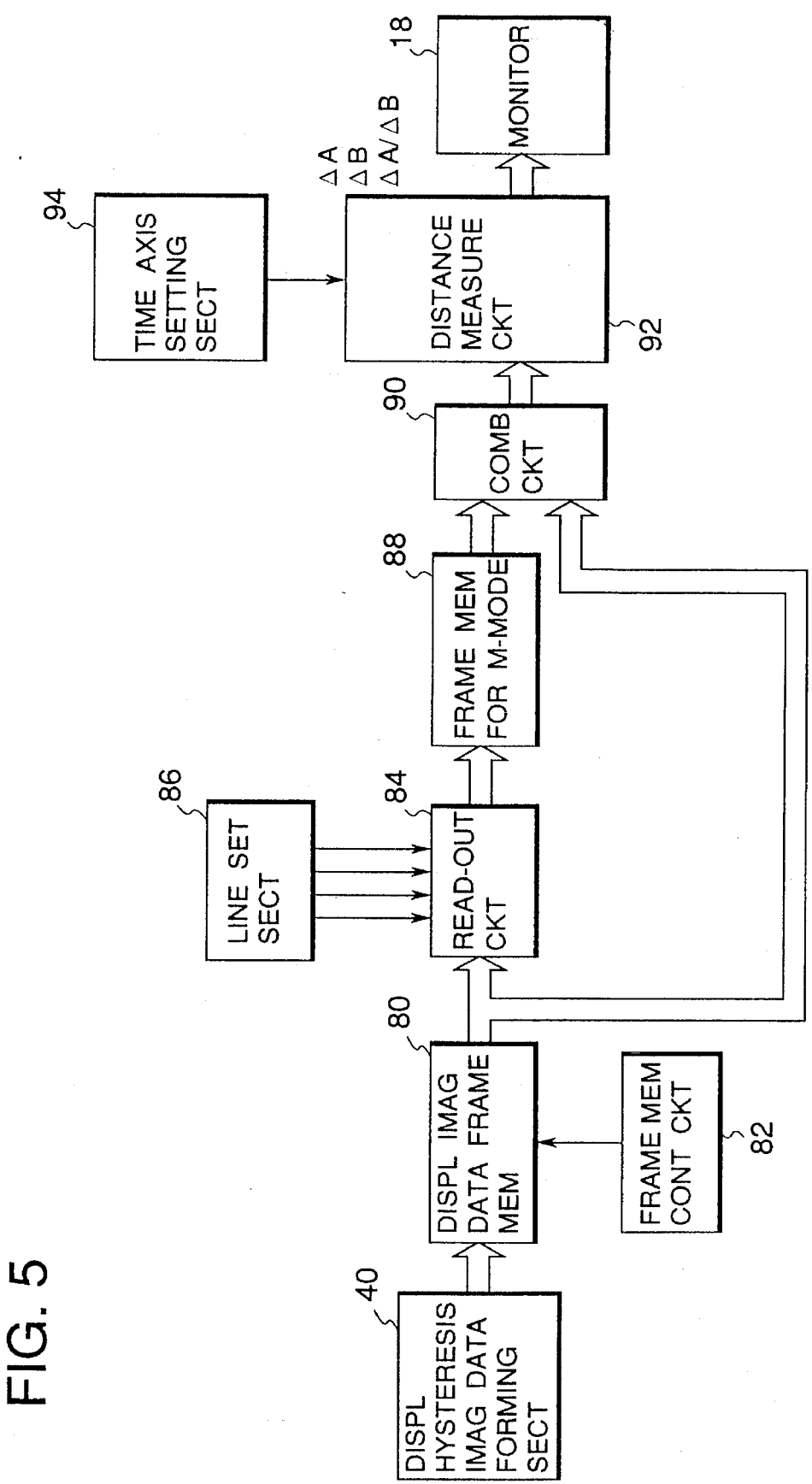
FIG. 5 is a block diagram showing the essential portions of a third embodiment of a diagnostic ultrasound apparatus according to the present invention.

The displacement hysteresis image data forming section 40 shown in FIG. 5 has the same structure as the displacement hysteresis image data forming section 40 shown in FIG. 1. The displacement hysteresis image data forming section 40 combines, with the lapse of time, displacement image data outputted from a displacement image data sampling circuit (not shown in FIG. 5) to form displacement hysteresis image data. This displacement hysteresis image data is then inputted into a displacement hysteresis image data frame memory 80. The frame memory 80 is controlled by a frame memory control circuit 82 and stores, frame by frame, the displacement hysteresis image data supplied from the displacement hysteresis image data forming section 40.

Figure 6:
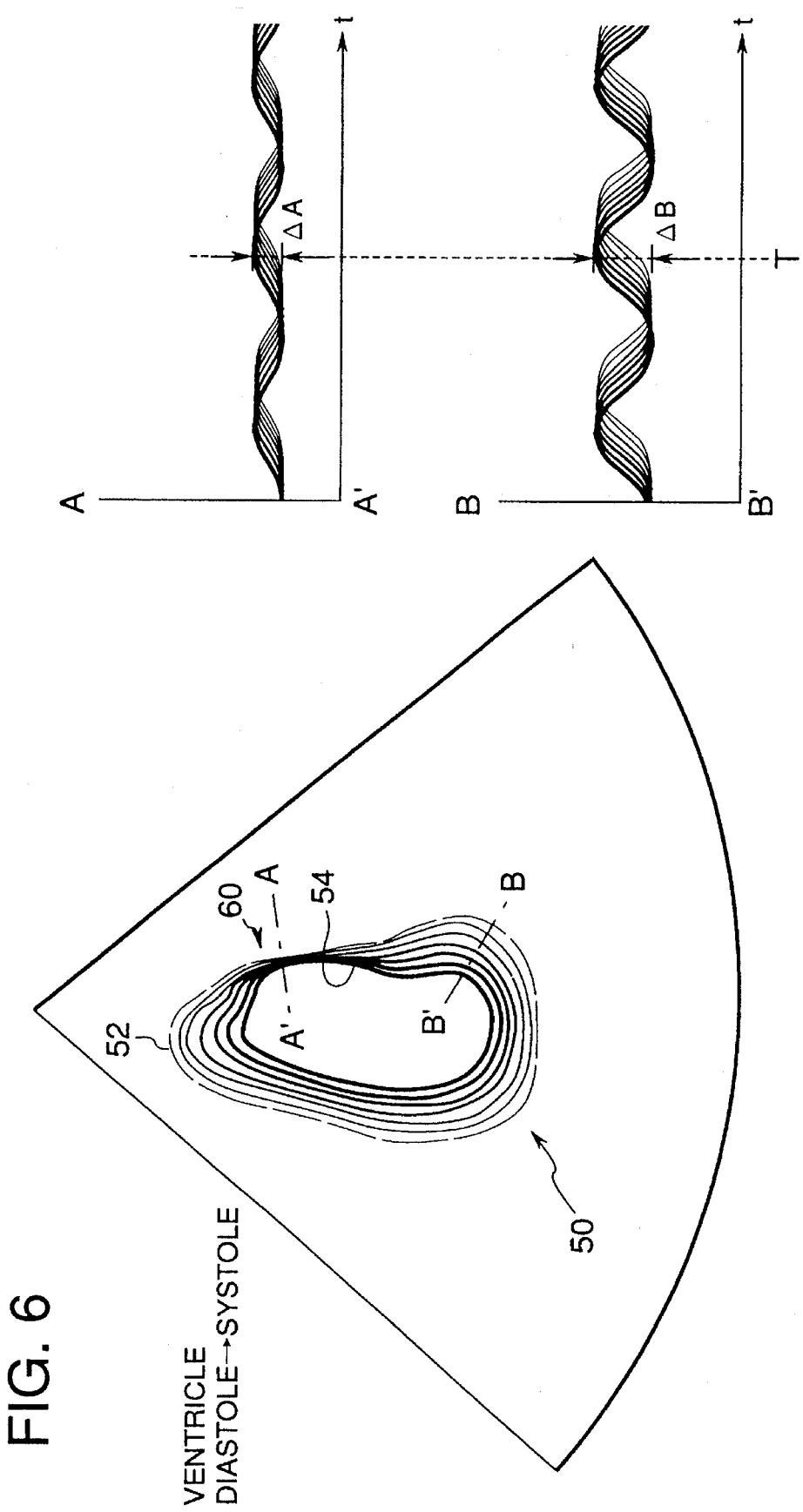
FIG. 6 is an example display of a displacement hysteresis image and M-mode images corresponding to freely designated lines according to the third embodiment of the diagnostic ultrasound apparatus according to the present invention.

The displacement hysteresis image data stored in the hysteresis image data frame memory 80 is first outputted to the monitor 18 via a combining circuit 90 and distance measuring circuit 92. At this point, a displacement hysteresis image 50 like that shown in FIG. 2 is displayed on the monitor 18. Then, an operator freezes (i.e., forms a still shot of) this displacement hysteresis image 50. Next, by using a line setting section 86, data sampling lines A—A' and B—B' are formed at desired positions and directions on the monitor 18, as shown in FIG. 6. In practice, the line setting portion 86 is constructed from a mouse, trackball, keyboard or the like.

The line data corresponding to the designated data sampling lines A—A', B—B' is inputted into a read out circuit 84 from the line setting portion 86. The read out circuit 84 selectively reads out from the displacement hysteresis image data frame memory 80 only the image data corresponding to the designated data sampling lines. The image data that has been read out is then read into an M-mode frame memory 88. Next, the image data that has been sampled along the designated data sampling lines A—A', B—B' by the read out circuit 84 is then sequentially inputted into the combining circuit 90. The image data inputted in this way is combined, when necessary, with displacement hysteresis image data directly inputted into the combining circuit 90 from the displacement hysteresis image data frame memory 80. In this case, as shown in FIG. 6, the displacement hysteresis image 50 and changes of image data with the lapse of time along the designated data sampling lines A—A', B—B' (hereinafter referred to as 'M-mode images') are displayed together on the same monitor 18. It is to be noted here that the designated data sampling lines need not be limited to two lines, as described above. In the case where a plurality of data sampling lines are designated, M-mode images taken along the plurality of designated data sampling lines can be simultaneously displayed on the monitor 18.

When the M-mode images are displayed, an operator can use a time axis setting section 94 shown in FIG. 5 to selectively designate an M-mode image time axis, such as a time axis having the lowest level of noise (time T in FIG. 6). Next, when a time axis has been designated, the distance measuring circuit 92 accordingly calculates the interval distances ΔA and ΔB based on image data corresponding to displacement hysteresis. Images along the selected time axis and then calculates the ratio ΔA/ΔB and the like. Then, the required values ΔA, ΔB, ΔA/ΔB and the like are displayed at prescribed regions on the monitor 18.

Now, if the diagnostic ultrasound apparatus of the third embodiment is constructed so as to be able to set the process time for sampling displacement image data in a manner similar to that described for the second embodiment, a more accurate calculation process can be carried out by the distance measuring circuit 92.

In this connection, FIG. 6 is an example display showing the outline of a displacement hysteresis image 50 during the period of time from the peak expansion of a heart ventricle to a peak contraction of the heart ventricle and changes (M-mode images) of ultrasound image data with the lapse of time along the data sampling lines A—A', B—B' designated for the displacement hysteresis image 50. In this case, in FIG. 6 the vertical axis represents distance and the horizontal axis represents time.

Furthermore, the width of displacement along the M-mode image (corresponding to the designated line A—A') in the region 60 of FIG. 6 where the contraction movement of the cardiac muscle is small is displayed as being smaller than the width of displacement of the M-mode image (corresponding to line B—B') in the region where the contraction movement is normal. By comparing these two M-mode images, it is possible to easily identify differences in movement depending on the part of the living body tissue being diagnosed. Moreover, by calculating the values of the widths ΔA, ΔB, and the ratio ΔA/ΔB along the prescribed time axis T for the two M-mode images, it is possible to use such values to more quantitatively ascertain the abnormal movement of the cardiac muscle (e.g. stenosis of coronary artery) in the region 60.

Figure 7:
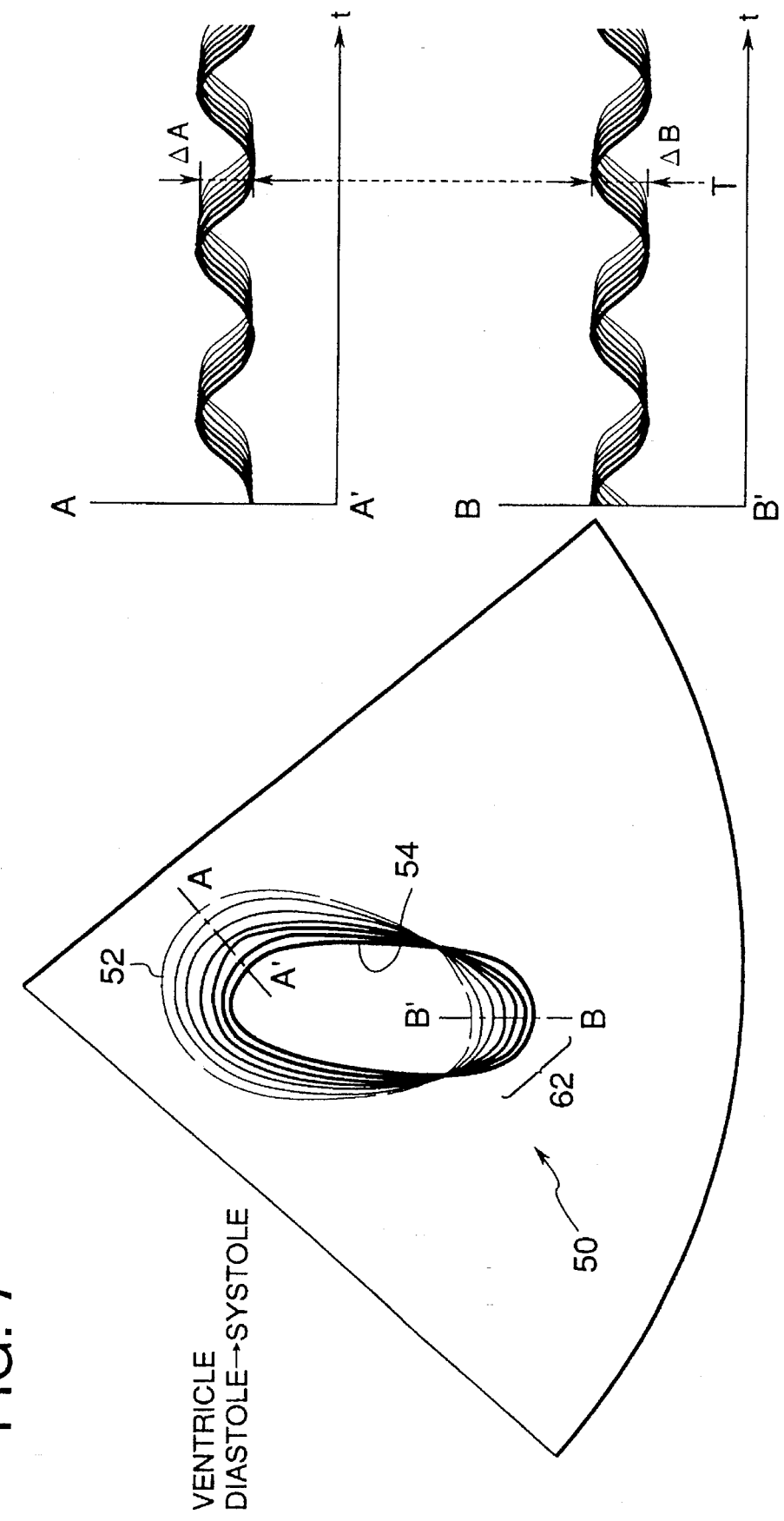
FIG. 7 is an example display of a displacement hysteresis image showing an abnormal movement of a heart ventricle that is different from that shown in FIG. 7 and M-mode images corresponding to freely designated lines.

FIG. 7 is an example display showing a displacement hysteresis image 50 and associated M-mode images for the case in which an abnormal movement, different from the abnormal movement shown in FIG. 6, arises during the time from the peak expansion in diastole of a heart ventricle to the peak contraction in systole of the heart ventricle.

As described above, for the displacement hysteresis image 50 in FIG. 7, the outermost displacement image 52 corresponding to the peak expansion of the heart ventricle is displayed with the lowest level of brightness, and successive displacement images are displayed with increasing levels of brightness. In this regard, the newest displacement image 54 corresponding to the peak contraction of the heart ventricle is displayed with the highest level of brightness among the displacement images of the displacement hysteresis image 50. If the heart ventricle moves in a normal direction, the displacement image 52 corresponding to the first state of contraction will be displayed at the outermost part of the displacement hysteresis image 50. Then, as the contraction of the heart ventricle progresses, each successive displacement image will be displayed steadily toward the inside of the displacement hysteresis image 50. Accordingly, the newest displacement image 54 will be displayed at the innermost part of the displacement hysteresis image 50.

However, if an abnormal movement occurs during the contraction stage that is the systole of the heart ventricle, such as when one portion of the heart wall protrudes outward (dyskinesis) during the systole, this will appear like the region 62 of the displacement hysteresis image 50 shown in FIG. 7. Namely, in the dyskinesis region 62, the newest displacement image 54 corresponding to peak contraction will be displayed outside the displacement image 52 corresponding to peak expansion. In this connection, if the displacement hysteresis image 50 is displayed under display conditions in which the sampling process time period for sampling displacement image data is set from the time of peak expansion to the time of peak contraction, as was previously described for the second embodiment, it becomes possible to easily detect the occurrence of dyskinesis in the heart ventricle. Furthermore, when the M-mode images are displayed for a normal region (along the designated data sampling line A—A') and the dyskinesis region 62 (along the designated data sampling line B—B') where movement occurs in an abnormal direction, it becomes easy to detect the mutual difference in phase for the two M-mode images. Accordingly, by comparing a plurality of M-mode images taken along a plurality of designated sampling lines, it becomes possible to determine the shift in phase of data relating to the direction of movement of their respective regions. Furthermore, if the phase difference of these M-mode images are calculated by the distance measuring circuit 92, it becomes possible to quantize the data relating to the movement of the living body tissue, and this contributes to the improvement of the accuracy of diagnosis.

In the third embodiment described above, when M-mode images taken along the designated lines on the displacement hysteresis image were displayed, the changes with the lapse of time over the entire tire period were displayed on the monitor 18. However, such M-mode image display need not be displayed for the entire time, For example, as was described with reference to the second embodiment, the M-mode images may be displayed only for a prescribed time interval. In such case, a sampling process having a prescribed time interval is carried out for sampling displacement image data. This results in the M-mode image being blank for the time interval in which the sampling process is not carried out. Furthermore, the read out circuit 84 of FIG. 5 may read out image data along a designated data sampling line of the newest displacement image data from the displacement image data sampling circuit 34 of FIG. 1 or FIG. 4, and then only the chances in this image data with the lapse of time may be displayed as M-mode images. In this case, as the amount of image data is small for each time of the M-mode images, there is the added advantage of the phase shift of the displayed M-mode images being easy to see.

In the above described embodiments, the descriptions were made mainly with regard to the cases where this invention is applied to diagnosis for heart of patients. However, use of this invention is not limited to the diagnosis of heart, and this invention can also be applied to diagnosis for other parts or regions of a living body such as blood vessels, for instance. In such a case, this invention is advantageous in finding arteriosclerosis, arterial embolism or the like.

Finally, it should be noted that the present invention is not limited to the embodiments described above. The spirit and scope of the present invention will be decided only by the following claims.

What is claimed is:

1. A diagnostic ultrasound apparatus, comprising:

a displacement image data frame memory for storing, frame by frame, two-dimensional ultrasound image data of a living body;

displacement image data sampling means for sampling displacement image data which is obtained by comparing two-dimensional ultrasound image data of a newest frame with the two-dimensional ultrasound image data of any one of the previous frames stored in the displacement image data frame memory, said displacement image data representing displacement in the living body between said compared frames;

displacement hysteresis image forming means for forming displacement hysteresis image data which represents changes over the thus-formed plural displacement image data by sequentially combining said plural displacement image data with the lapse of time; and display means for displaying a displacement hysteresis image on the basis of said displacement hysteresis image data.

2. The diagnostic ultrasound apparatus as claimed in claim 1, wherein said displacement image data is produced by comparing the two-dimensional ultrasound image data of the newest frame with the two-dimensional ultrasound image data of the previous frame just before the newest frame and then sampling portions of both data which are different from each other.

3. The diagnostic ultrasound apparatus as claimed in claim 1, wherein said displacement image data frame memory stores two-dimensional ultrasound image data of a plurality of previous frames, and said displacement image data is produced by comparing the two-dimensional ultrasound image data of the newest frame with the two-dimensional ultrasound image data of a fixed one of the previous frames, and then sampling portions of both data which are different from each other.

4. The diagnostic ultrasound apparatus as claimed in claim 1, wherein said displacement hysteresis image forming means includes displacement hysteresis image frame memory for storing said plural displacement image data, and means for adding said plural displacement image data stored in said displacement hysteresis image frame memory with a newest displacement image data supplied from said displacement image data sampling means to form said displacement hysteresis image data.

5. The diagnostic ultrasound apparatus as claimed in claim 4, wherein said displacement hysteresis image forming means further includes means for imparting weighting on each of said plural displacement image data stored in said displacement hysteresis image frame memory for distinguishing each of said plural displacement image data.

6. The diagnostic ultrasound apparatus as claimed in claim 5, wherein said two-dimensional ultrasound image data is formed from brightness data, and said weighting process is carried out so as to reduce the brightness value of the respective previous displacement image data gradually in comparison with that of the newest one.

7. Tho diagnostic ultrasound apparatus as claimed in claim 1, further comprising means for thresholding said two-dimensional ultrasound image data which is to be supplied to said displacement image data frame memory into binary-coded image data on the basis of a predetermined threshold value, and said displacement image data is formed from said binary-coded two-dimensional ultrasound image data.

8. The diagnostic ultrasound apparatus as claimed in claim 7, further comprising means for eliminating noise from said binary coded two-dimensional image data, and such noise-eliminated data being outputted to said displacement image data sampling means and said displacement image data frame memory.

9. The diagnostic ultrasound apparatus of claim 1, further comprising sampling control means for controlling the process time of the displacement image data sampling process carried out by the displacement image data sampling means.

10. The diagnostic ultrasound apparatus as claimed in claim 9, wherein said processing time is synchronized with biological signals of the living body.

11. The diagnostic ultrasound apparatus as claimed in claim 10, wherein said processing time is synchronized with the occurrences of the R-waves of a heart of the living body.

12. The diagnostic ultrasound apparatus as claimed in claim 1, further comprising means for setting at least one desired data sampling line for said displacement hysteresis image displayed on said display means, means for sampling ultrasound image data along said data sampling line from the displacement hysteresis image data constituting said displacement hysteresis image, and means for displaying said sampled data on said display means with the lapse of time as M-mode image.

13. The diagnostic ultrasound apparatus as claimed in claim 12, wherein said ultrasound image data sampling means includes means for storing said displacement hysteresis image data, and means for selectively reading out said ultrasound image data corresponding to said ultrasound image data along said data sampling line from said storing means.

14. The diagnostic ultrasound apparatus as claimed in claim 13, further comprising means for measuring the width of the M-mode image at a designated time axis which shows the amount of the displacement along the data sampling line.

15. A diagnostic ultrasound apparatus, comprising:
means for recording, frame by frame, two-dimensional ultrasound image data obtained by transmitting and receiving ultrasound waves to and from an object to be observed of a living body;
means for producing displacement image data on the basis of two-dimensional ultrasound image data of a newest frame and the two-dimensional ultrasound image data of any one of the previous frames stored in said recording means, said displacement image data representing the displacement of the object between said newest frame and said previous one frame;
means for producing composite image data which represents the amount of the movement of the object to be observed for a certain period, by sequentially combining the thus-obtained plural displacement image data for the certain time period, said composite image data being visible as a single image; and
means for displaying said composite imaged data.

16. A diagnostic ultrasound apparatus, comprising:
means for recording, frame by frame, plural two-dimensional ultrasound image data of different stages of movement of an object to be observed of a living body;
means for producing composite ultrasound image data which can represent as a single image the movement of the object with a lapse of time over a certain period, said composite ultrasound image data being formed by using said plural ultrasound image data recorded in said recording means and two-dimensional ultrasound image data of a newest frame; and
means for displaying the thus-produced composite ultrasound image data.

17. A method of observing an object of a living body with ultrasound waves, comprising the steps of:
transmitting and receiving ultrasound waves to and from the object of the living body to be observed;
recording, frame by frame, two-dimensional ultrasound image data obtained from the received ultrasound waves into a frame memory;
producing displacement image data by comparing two-dimensional ultrasound image data of a newest frame with the two-dimensional ultrasound image data of any one of the previous frames stored in said frame memory, thus forming displacement image data constituting a displacement image which represents the displacement amount of the object between these frames;
producing displacement hysteresis image data which represents changes of the object between said plural displacement images by sequentially combining said plural displacement image data with the lapse of time; and displaying thus-formed displacement hysteresis image data on a monitor for the purpose of observation.

18. The method as claimed in claim 17, further comprising the step of changing the brightness of each of the displacement image data.

19. A method of diagnosing a heart of a patient with ultrasound waves, comprising the steps of:

producing plurality of B-mode image data of the heart of the patient to be diagnosed, and storing these image data into a frame memory;

producing plural displacement image data which represents the displacement of a cardiac muscle of the heart by using B-mode image data of a newest frame and any one of the previous B-mode image data stored in the frame memory;

combining thus-obtained plural displacement image data into one image data to form a composite image which represents the movement of the cardiac muscle with a lapse of time for a certain interval, in which a portion of the heart having a small movement is indicated by a small width, and then displaying said composite image as a single image; and inspecting the condition of the heart of the patient on the basis of said displayed composite image.

20. A diagnostic ultrasound apparatus, comprising:

means for obtaining B-mode image data by transmitting and receiving ultrasound waves to and from an object of a living body to be observed;

means for producing composite image data which represents the sequential displacement of the object with a lapse of time for a certain period, said composite image data being obtained by sequentially combining thus-obtained plural B-mode image data with the lapse of time for the certain period; and means for displaying thus-formed composite image data as a composite image which is displayed in a single image.

21. A diagnostic ultrasound apparatus comprising:

means for obtaining B-mode image data by transmitting and receiving ultrasound waves to and from an object of a living body to be observed;

means for producing composite image data which represents the displacement of the object for a certain period, said composite image data being obtained by sequentially combining thus-obtained plural B-mode image data with the lapse of time for the certain period;

means for displaying thus-formed composite image data as a composite image; and means for thresholding said B-mode image data into binary-coded image data.

22. The diagnostic ultrasound apparatus as claimed in claim 21, further comprising:

frame memory means for recording said plural binary-coded B-mode image data frame by frame; and means for producing displacement image data which represents displacement of the object between any one of the previous frame stored in said frame memory and a newest frame, said displacement image data being formed on the basis of the B-mode image data of said previous frame and B-mode image data of said newest frame; wherein thus-obtained a plurality of said displacement image data being sequentially combined for the time period to form said composite image data.

23. The diagnostic ultrasound apparatus as claimed in claim 22, further comprising means for distinguishing each of said plural displacement image data which form said composite image data.

* * * * *

UNITED STATES PATENT AND TRADEMARK OFFICE
CERTIFICATE OF CORRECTION

PATENT NO. : 5,515,849
DATED      : May 14, 1996
INVENTOR(S) : Murashita et al.

It is certified that error appears in the above-identified patent and that said Letters Patent is hereby corrected as shown below:

Column 2, line 9, "time present" should read --the present--;
Column 4, line 40, "at tiler time" should read --at that time--;
Column 7, line 33, "circuit 38" should read --circuit 36--;
Column 7, line 47, "memory 48" should read --memory 46--;
Column 8, line 14, "section 18" should read --section 13--;
Column 10, line 27, "memory 48" should read --memory 46--;
Column 10, line 33, "at time next" should read --at the next--;
Column 10, line 59, "image" should read --image 54--;
Column 11, line 52, "comparison which prior" should read --comparison with prior--;
Column 11, line 63, "risk off injury" should read --risk of injury--;
Column 14, line 53, "all operator" should read --an operator--.

Signed and Sealed this

First Day of June, 1999

Attest:

Q. TODD DICKINSON

*Attesting Officer*          *Acting Commissioner of Patents and Trademarks*